(12) United States Patent
Mainardi

(10) Patent No.: US 11,554,162 B2
(45) Date of Patent: Jan. 17, 2023

(54) PHARMACEUTICAL OR FOOD SUPPLEMENT PREPARATION BASED ON ALPHA-LACTALBUMIN

(71) Applicant: KOLFARMA S.R.L., Genoa (IT)

(72) Inventor: Paolo Mainardi, Genoa (IT)

(73) Assignee: KOLFARMA S.R.L., Genoa (IT)

( * ) Notice: Subject to any disclaimer, the term of this patent is extended or adjusted under 35 U.S.C. 154(b) by 53 days.

(21) Appl. No.: 16/979,912

(22) PCT Filed: Mar. 13, 2019

(86) PCT No.: PCT/EP2019/056336
§ 371 (c)(1),
(2) Date: Sep. 11, 2020

(87) PCT Pub. No.: WO2019/175274
PCT Pub. Date: Sep. 19, 2019

(65) Prior Publication Data
US 2021/0361748 A1    Nov. 25, 2021

(30) Foreign Application Priority Data

Mar. 14, 2018  (IT) .................. 102018000003557

(51) Int. Cl.
| | | |
|---|---|---|
| *A61K 38/38* | (2006.01) | |
| *A61K 33/06* | (2006.01) | |
| *A61K 9/00* | (2006.01) | |
| *A61K 9/16* | (2006.01) | |
| *A61P 25/08* | (2006.01) | |
| *A61P 25/16* | (2006.01) | |
| *A61P 25/24* | (2006.01) | |
| *A23L 33/12* | (2016.01) | |
| *A23L 33/15* | (2016.01) | |
| *A23L 33/16* | (2016.01) | |
| *A23L 33/18* | (2016.01) | |
| *A61K 31/19* | (2006.01) | |

(52) U.S. Cl.
CPC .............. *A61K 38/38* (2013.01); *A23L 33/12* (2016.08); *A23L 33/15* (2016.08); *A23L 33/16* (2016.08); *A23L 33/18* (2016.08); *A61K 9/0053* (2013.01); *A61K 31/19* (2013.01); *A61K 33/06* (2013.01); *A61P 25/08* (2018.01); *A61K 9/1611* (2013.01); *A61K 9/1623* (2013.01); *A61K 9/1664* (2013.01)

(58) Field of Classification Search
CPC .... A61K 2300/00; A61K 31/19; A61K 31/25; A61K 38/38; A61K 33/06; A61K 9/0053; A61K 9/145; A61K 9/1611; A61K 9/1617; A61K 9/1623; A61K 9/1664; A23L 33/12; A23L 33/15; A23L 33/16; A23L 33/18; A61P 25/08; A61P 25/16; A61P 25/24

See application file for complete search history.

(56) References Cited

U.S. PATENT DOCUMENTS

| 6,096,870 A | 8/2000 | Mozaffar et al. |
|---|---|---|
| 2003/0185917 A1* | 10/2003 | Salimath ................. A61K 45/06 514/557 |
| 2010/0168233 A1* | 7/2010 | Jayes ................... A61K 9/0009 514/557 |

FOREIGN PATENT DOCUMENTS

| CN | 105746711 A | 7/2016 |
|---|---|---|
| EP | 2218462 A1 | 8/2010 |
| WO | 2008138348 A1 | 11/2008 |

OTHER PUBLICATIONS

Zhang et al., "Converting Peptides into Drug Leads by Lipidation," Current Medicinal Chemistry, 2012, 19: 1602-1618. (Year: 2012).*
Search Report and Written Opinion of PCT/EP2019/056336 dated Jun. 13, 2019.

* cited by examiner

*Primary Examiner* — Julie Ha
(74) *Attorney, Agent, or Firm* — Silvia Salvadori, P.C.; Silvia Salvadori

(57) ABSTRACT

Pharmaceutical or food supplement preparation including alpha-lactalbumin and at least one short-chain fatty acid (SCFA) or a precursor or derivative thereof for use in the treatment of disorders of the central nervous system; the SCFA or its precursor or derivative may be contained in at least one first dosage unit together with a carrier acceptable from the pharmaceutical or food standpoint and the alpha-lactalbumin in at least one second dosage unit together with a carrier acceptable from the pharmaceutical or food standpoint, and said dosage units may be distinct units intended for simultaneous or separate administration or the preparation may consist of a pharmaceutical or food supplement composition comprising the at least one short-chain fatty acid or a precursor or derivative thereof and alpha-lactalbumin together with a carrier acceptable from the pharmaceutical or food standpoint.

18 Claims, 1 Drawing Sheet

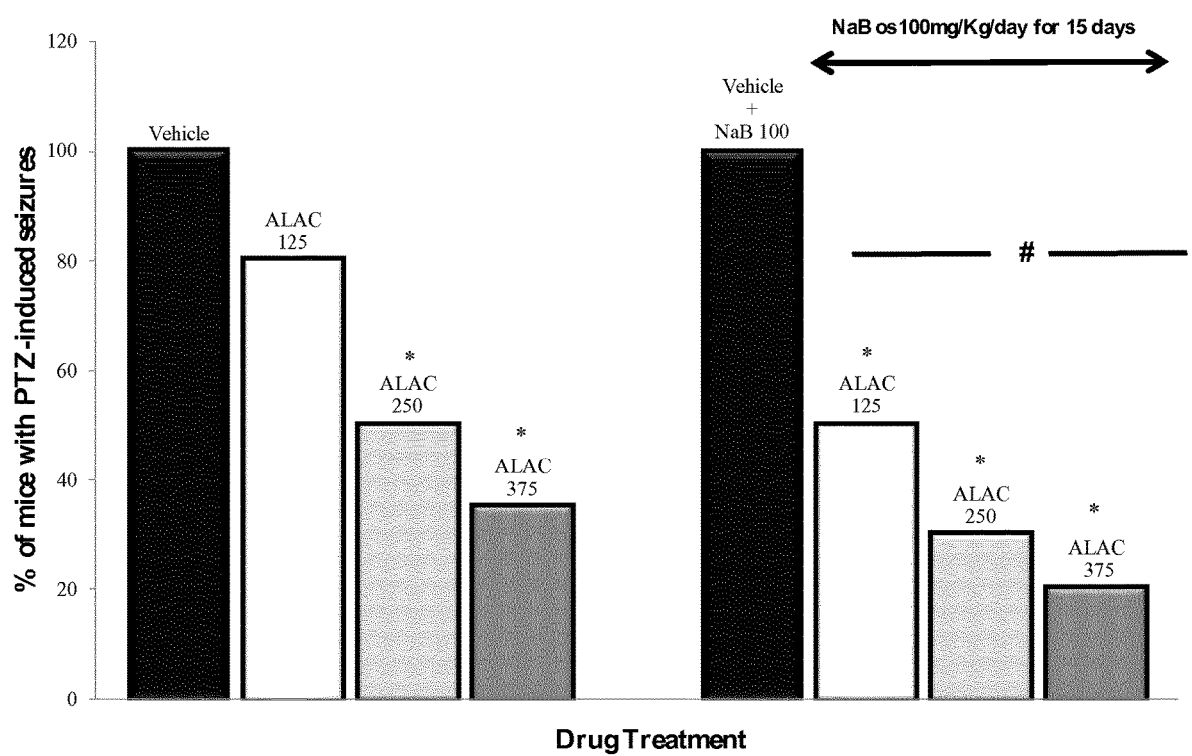
*significant with respect to the relevant control group

PHARMACEUTICAL OR FOOD SUPPLEMENT PREPARATION BASED ON ALPHA-LACTALBUMIN

This application is a U.S. national stage of PCT/EP2019/056336 filed on 13 Mar. 2019, which claims priority to and the benefit of Italian Patent Application No. 102018000003557 filed on 14 Mar. 2018, the contents of which are all incorporated herein by reference in their entireties.

FIELD OF APPLICATION

The present invention relates to the technical field of the pharmaceutical industry or food supplement industry.

In particular, the invention relates to a pharmaceutical or food supplement preparation containing alpha-lactalbumin and at least one short-chain fatty acid or a precursor or derivative thereof.

PRIOR ART

Recently, alpha-lactalbumin has been proposed as food supplement mainly because of its brain serotonergic action.

Italian Patent Application N. GE2006A000013 on behalf of the Applicant relates indeed to the use of alpha-lactalbumin in the treatment of neurological and neuropsychiatric disorders, such as Parkinson's disease, depressive disorders and epilepsy and European Patent N. EP 2 218 462 B1 relates to a pharmaceutical preparation comprising a SSRI or a SSNRI and alpha-lactalbumin for the treatment of depressive disorders.

Role of Serotonin

Serotonin is a tryptamine, synthesized from the essential amino acid tryptophan, mostly produced by enterochromaffin cells in the gastrointestinal tract, where it takes part to several biological functions, and by the serotonergic neurons of the central nervous system.

At peripheral level, it plays several control functions. In the gastrointestinal tract it controls peristalsis, fluids secretion, it controls nausea and vomiting. It has vasoconstrictive action on blood vessels, even the intracranial ones, whose dilation contributes to migraine. It controls platelets aggregation, repairing processes and homeostasis processes [1, 2], regeneration processes of liver [3], heart [4], and it controls the thermogenesis.

In the central nervous system too, serotonin plays several functions, which comprise regulation of mood, sleep, body temperature, sexuality, empathy, cognitive functions, creativity and appetite.

It is thought that pathological alterations in functionality of serotonin circuitry are involved in several neurological and neuropsychiatric disorders such as migraine, obsessive-compulsive disorder, depression, schizophrenia, anxiety, mood disorders of any kind, food disorders (emotional eating and bulimia), male premature ejaculation and fibromyalgia.

Serotonin is thus central in the mechanism of action of several psychotropic drugs, especially antidepressants (such as for example the antidepressants SSRIs as Dropaxin, Prozac and Zoloft, tricyclic antidepressants and monoamine-oxidase inhibitors) and antipsychotics.

Recent studies reconsidered the role of serotonin in epilepsy [5, 6], turning it from proconvulsant into anticonvulsant [7, 8, 9]. It seems that the serotonergic and noradrenergic system is the linking element between both the physiopathogenetic mechanisms of depression and of epilepsy [10, 11], and between the mechanisms of action of antidepressant drugs and antiepileptic drugs [12], thus reconfirming the role of these two neurotransmitters in the pathogenesis of depression, as it was suggested by the first studies on the concentration of their catabolites in urine and/or cerebrospinal fluid. A potentiation of serotonin would thus facilitate, at a brain level, controlling epileptic seizures [13], and other functions which are controlled by serotonin, and similarly for those controlled at peripheral level.

Tryptophan as Serotonin Precursor

At both the peripheral level and in the central nervous system, serotonin is synthesized from the essential amino acid Tryptophan, since plasma serotonin is not able to overcome the blood-brain barrier, while Tryptophan is able to pass through the blood-brain barrier thanks to an active transporter which is shared with all the "Large Neutral Amino Acids" (LNAAs) to which tryptophan belongs. This competition for cerebral uptake results in the rate of synthesis of brain serotonin, which depends on the amount of Tryptophan uptake, being influenced by the plasma ratio between this amino acid and the sum of all its competitors (Trp/LNAAs) [14]. On this base, a reduction by one third of the rate of synthesis of brain serotonin compared to healthy controls was assessed from the measurements of the plasma Trp/LNAAs ratios in a group of epileptic patients. (15).

How to Increase Trp and Therefore Serotonin

Oral administration of tryptophan does not result in a plasmatic increase of the Trp/LNAAs ratio, given the low bioavailability of the single amino acids. The plasmatic essential amino acids only derive from the demolition of dietary protein [16].

Among all proteins, whey proteins are the ones able to provide a higher increase of plasma levels of amino acids because, since they do not precipitate in the acidic environment of the stomach, they are demolished into peptides, which easily pass through the intestinal membrane. Then, the demolition into single amino acids continues in the blood. Due to the high speed of their digestive process, they are referred to as "fast-protein". The other proteins, instead, precipitate into the stomach and the enzymes take from the precipitate primarily single, scarcely bioavailable amino acids, [17]. The bioavailability of alpha-lactalbumin is maximal (=1). In particular, alpha-lactalbumin is demolished into medium-small peptides in the stomach after only 15 minutes from oral administration, and such peptides then enter into the small intestine.

The best way to increase the plasma Trp/LNAAs ratio seems to be to take a whey protein which is rich in Trp and poor in its competitor LNAAs.

On these bases alpha-lactalbumin was selected as serotonergic agent, since it is "rich" in tryptophan and poor in its competitors for cerebral uptake, the LNAAs, (18).

Unexpected Finding: Plasma TRP/LNNA Profile

Contrary to the expectations (resulting from the hypothesis of an increase of TRP consequent to its release from alpha-lactalbumin), the results obtained in both experimental and clinical studies show that the increase of plasma tryptophan/LNAAs ratio is not due to tryptophan deriving from the demolition of alpha-lactalbumin. In fact, given the fast absorption, a fast plasmatic peak of amino acids constituting alpha-lactalbumin, with a fast return to basal values within about 20-30 minutes from the administration should be observed.

Instead, studies in which alpha-lactalbumin administrations were repeated for several days show that the plasma Trp/LNAAs ratio continues to increase over the time, tending to an asymptotic value between 0.22-0.23. [19]

Similar results have been obtained by the Applicant on experimental models of epilepsy [20]. FIG. 1, attached, shows in a plot the time course of the plasma Trp/LNAAs ratio after several consecutive days of oral administration of alpha-lactalbumin; N=7 in each group, data expressed as mean±SEM.

The time course of the plasma Trp/LNAAs ratio observed is representative of specific actions of alpha-lactalbumin in the whole digestive system, suitable to reduce an intestinal dysbiosis, which is responsible for excessive decarboxylation of tryptophan into indole and skatole, and therefore to increase the capability to obtain tryptophan from dietary proteins.

Also the results obtained both in experimental models and in clinical trials confirm the need of repeated administrations for several days. In different experimental models of epilepsy the protective action against seizures was observed to occur after at least 6 days of repeated administrations, and not to increase when continuing administrations (up to 12 days). Moreover, it does not seem to depend on the administered dose. FIG. 2 shows indeed the time courses of the protection against audiogenic seizures in genetically epilepsy-prone-9 rats (GEPRs: n=5 animals for group of dose and time); (A) results after 5 consecutive days of treatment; (B) results after 12 consecutive days of treatment. The diagram shows medians±the interquartile range for each group.

Moreover, after three weeks of treatment, the protective effect against seizures, which are induced by means of acoustic stimulation in audiogenic mice, continues for at least one month from the suspension of treatment, confirming that the specific actions produce modifications which are stable over time and independent of the administration. (21)

In humans too it is observed that consecutive administrations are required to obtain the clinical effect, which suggests that the clinical results are due to intestinal specific actions of alpha-lactalbumin apt to reduce dysbiosis and inflammation and not just to a tryptophan release.

Intestinal Actions of Alpha-Lactalbumin

On the other side, alpha-lactalbumin is much expressed in colostrum of humans, and only of humans, where it plays specific actions on the digestive system, apt to activate it with the first breastfeeding.

In the literature it is reported that alpha-lactalbumin enhances all gastric processes: it increases prostaglandins, mucus and mucin secretion, gastric emptying [22] and secretion of bicarbonate and acid from proton pumps, thereby restoring a correct intestinal pH, on which a correct symbiosis of the microbiota depends.

The intestinal prebiotic actions are highlighted by the capability to protect the digestive system from ulcers induced by stress or alcohol: after an administration of an alpha-lactalbumin dose, a same amount of ingested alcohol does not produce gastric ulcers anymore [23].

Alpha-lactalbumin also restores a correct inflammatory response [24], reduces intestinal membrane permeability and has an intestinal antibacterial action [25].

As a whole, all these actions contribute to reduce an intestinal dysbiosis, responsible for an excessive demolition (decarboxylation) of tryptophan into indole and skatole. In fact, administering proteins rich in tryptophan, such as *Griffonia* or *Hypericum perforatum*, in subjects affected by intestinal dysbiosis, results in an increase of urinary levels of indole and skatole, not of plasma tryptophan. (26)

The Applicant has instead surprisingly found, by measuring the urinary levels of indole and skatole, a progressive reduction of said levels during a chronic treatment with alpha-lactalbumin.

Evidence of the Role of Peptides Deriving from the Digestion of Alpha-Lactalbumin From these observations it appears clear that the specific actions of alpha-lactalbumin on the whole digestive tract are not produced by the whey protein as such, but by its peptide fractions deriving from its rapid demolition in the stomach. As a further evidence of this, it is to be noted that, when alpha-lactalbumin is ingested with colostrum, the newborn produces specific salivary enzymes to digest it, since his/her stomach is still not able to do it. The digestive system has indeed formed during intrauterine life, but has never worked before the first breastfeeding. Salivary digestion of alpha-lactalbumin produces the specific peptides which have the task to activate the digestive system of humans, and only of humans, stimulating the production of all what is necessary to process the food and to protect the digestive tract tissues. Once the digestive system has been activated, the newborn stops producing the salivary specific enzymes and the digestive function is transferred to the stomach, which gradually learns how to process other, more complex food during weaning.

From this results that the oral administration of alpha-lactalbumin in a weak digestive system, with a reduced demolition capability, may cause the formation of peptide fractions other than the functional ones, and that the correct peptide fractions may not produce appropriate responses if the cells of the digestive system are hyporesponsive, since malnourished. Also an intestinal inflammation, especially a chronic, low-level inflammation, also due to a weakness of the digestive system in dealing with complex food, reduces the possibility to correctly demolish alpha-lactalbumin and, thus, to obtain from it the correct peptides with specific actions onto the digestive system of humans. Moreover, the inflammation is associated and/or lead to intestinal dysbiosis, being inflammation and dysbiosis two sides of the same coin.

Observed Limitations: Alpha-Lactalbumin does not Operate in Weak Digestive Systems The experience of the Applicant about the use of alpha-lactalbumin as food supplement showed that it surprisingly has difficulty to operate in subjects with a really weak digestive system, for example because its cells are malnourished. Said observation was evident especially in subjects who had experienced for a long period deprivation diets, often exactly induced by the inability to process complex food. This kind of diets weakens the digestive system, which becomes weaker and weaker in processing food and thus results in a progressive increase of the kinds of non-tolerated food.

The continuous increase of the incidence of disorders like allergies, food intolerances and autoimmune disorders shows a scenario of digestive systems which are weaker and weaker in relation to food made more and more aggressive also because of treatments with ionizing radiation. At the same time, wrong dietary recommendations, not supported by scientific evidence, contributed to weaken the digestive system of humans.

The only way to infer which is the correct diet for humans is to know the physiology of the digestive system, to compare it with the ones of other mammalians and to take into account the large modifications it has experienced during the evolutionary process.

Thanks to the recent findings about the microbial world, which co-exists in the human body, we have understood that the primary task of the digestive system is to maintain a comfortable environment for anaerobic bacteria living in the colon, not to feed us. It is obvious that, to operate correctly, its cells have to be fed. The only feeding for the cells of all digestive systems are Short Chain Fatty Acids (SCFAs), which are obtained in a different way, according to the different food preferences, from different digestive machinery in the different mammalians.

Since humans descend from apes, their digestive system was similar to the one of frugivores, consisting of a small stomach which constitutes 15% of the system and a long colon, which constitutes 60% of the system. In fact, frugivore animals eat fibers and, among them, the indigestible fibers reach the colon, where they are fermented by the bacteria living therein and transformed into SCFAs. Rodents obtain the precious SCFAs from fermentation of cellulose in the cecum, which is greatly developed in their digestive system, while in humans it is atrophied (appendix). Predatory carnivores, who preferably eat entrails of the killed animal which contain a 60% saturated fats, directly obtain SCFAs by cutting the fats by means of a strong lipase and of a large stomach, which constitutes 70% of their digestive system, while their colon is only 10% of the digestive system. Necrophagous carnivores eat low-fat meat, but only after it has been strongly decomposed/digested by environmental bacteria. Humans, who were initially frugivores, have learnt over the course of their evolution to obtain SCFAs also from saturated fats, especially from meat saturated fats, besides from fibers. The introduction of more aggressive food (not only meat) compared to that for which the digestive system of humans was designed, caused a reduction of the intestine to reduce the time of contact between said food and the intestine itself. More energy is therefore available for the brain, which has thus grown in size, developing from Neanderthal to *Sapiens Sapiens*. The colon has reduced to a 15% of the digestive system compared to the initial 60%. The stomach remained 15% of the digestive system also after introducing meat, while the small intestine has extended to give to a lipase weaker than the carnivores' one the time to cut saturated fatty acids. Therefore, with the existent digestive system, even if humans should ingest the same fiber amount as a frugivore, they could not obtain sufficient specific nutrients of the digestive system, (the SCFAs), given the small number of bacteria living in the colon.

This is probably the reason for which previous clinical experiences of the Applicant, directed to improve the action of alpha-lactalbumin in patients with weak digestive system, by means of concomitant administration of oligofructosaccharides, inulin or other prebiotic fibers, have shown not fully satisfying results.

Humans could survive because they have learnt to obtain short-chain fatty acids from saturated fats besides from fibers; shortening of the colon from 60% to 15% proves that they preferred this second way.

However, the condemnation of saturated fats, unjustly accused to be responsible of a dangerous increase of the plasma level of cholesterol, which is not a fat but an alcohol and which for 80% does not derive from diet, has reduced the capability to produce SCFAs and therefore to feed the cells of the digestive system. In addition, there is plenty of literature which highlights the risk of reducing not only total cholesterol, but also only LDL.

Short-chain fatty acids (SCFAs) are, from the most to the least nourishing: butyric acid, acetic acid, propionic acid and valeric acid.

SCFAs, besides being specific nutrients, increase intestinal motility stimulating serotonin synthesis [27], pass through the intestinal epithelium and go into the blood where they carry out cell signalling mechanisms: histone deacetylase (HDACs) inhibition [28] and activation of G-protein-coupled receptors (GPCRs).

HDACs regulates gene expression, its inhibition results in a broad range of consequences which still have mostly to be understood. GPCRs have been identified as receptors for SCFAs and they are involved in the regulation of metabolism and inflammation [29] SCFAs alter chemotaxis, phagocytosis, induce ROS, modify cellular proliferation, have anti-inflammatory, antitumoral and antimicrobial actions. They play an important role in maintaining intestinal and immune homeostasis [30].

The action on inflammatory processes by SCFAs is confirmed by the fact that a class of NSAIDs consists of synthetic derivatives of acetic and propionic acid, highlighting that the inhibitory action on HDASs may contribute to their anti-inflammatory action. The inhibitory action of butyric acid is found to be higher than that of acetic and propionic acid.

The use of butyric acid has been proposed in autoimmune and inflammatory disorders [31], against bacterial infections [32], to reduce cellular proliferation in colon cancers [33] and to reduce glycemia, insulin-resistance, dyslipidemia and gluconeogenesis in comparison with metformin [34, 35, 36]. Butyric acid shows protective action in experimental models of spinal muscular atrophy [37], as well as it reduces muscle atrophy during aging [38], has therapeutic action on allergic rhinitis [39], improves heart functions [40], decreases alcohol intake in dependent animals [41] and protects against severe burn-induced remote acute lung injury [42].

In the light of the recent literature it is therefore thought that many actions are due to a single effect onto the intestinal microbiota, resulting in a reduction of inflammation [43, 44].

Nowadays it is no more surprising that cerebral actions may correspond to this intestinal action, such as behavioral improvements of depressive anxious states [45, 46], of cognitive functions [47, 48], of stress responses [49], attenuation of autistic behaviors [50], manic psychoses [51]. Since the cerebral uptake was measured being of the order of 0.006% [52], it is clear that to influence brain processes it does not need to enter into the brain, but it may act onto the peripheral nervous system and onto the immune system.

The SCFAs receptors are important regulators of immunological functions, including neuroinflammation, energy metabolism, endocrine regulation of physiology and of behavior. The responses observed in psychiatric disorders, including depression, to a histone hyperacetylation induced by butyrate, such as an attenuation of depressive behavior in experimental models [53], may depend on an increase of the BDNF level in specific brain regions, such as the prefrontal cortex [54], which is probably due to an increased acetylation in BDNF gene [55].

WO 2008/138348 discloses a complex comprising alpha-lactalbumin and a fatty acid or a lipid suitable for use in the manufacture of medicaments for treating respiratory tract infections, cancer and warts and for the inhibition of angiogenesis.

U.S. Pat. No. 6,096,870 discloses a method for the separation of whey proteins through the use of chromatography and mentions the elution of alpha-lactalbumin from a ionic exchange column with a sodium acetate solution.

CN 105 746 711 discloses a milk-based product for improving sleep, which contains, among the other ingredients, gamma-amino-butyric acid.

The experience of the Applicant in the use of alpha-lactalbumin as a food supplement showed that it is possible to regain a clinical response by means of the association of a complex dietary protocol capable of enhancing the digestive system of humans and thereby making it more responsive to alpha-lactalbumin stimulations and consequently increasing tryptophan absorption and serotonin synthesis, with the consequent advantages in preventing and treating the above-mentioned disorders and in general all disorders wherein tissue inflammation is reported to be the physiopathogenic cause, since this inflammation derives from an intestinal chronic, low-degree inflammation [56].

These intestinal prebiotic actions are nowadays of great interest for treating disorders, especially neurological disorders, because of the stronger and stronger evidence of the role of the intestine-brain axis [30], but also because of the growing evidence of the role of microbiota in tipping the scale towards a healthy or a disease state [57].

Therefore, the Applicant addressed the problem to boost alpha-lactalbumin efficacy for treating the above-mentioned disorders and hypothesized, as a solution to said problem, to obtain an amelioration of the conditions of the digestive system, giving to it a correct nourishment and reducing inflammation in it.

The problem was solved, according to the present invention, providing a pharmaceutical or food supplement preparation including alpha-lactalbumin and at least one short-chain fatty acid or a precursor or derivative thereof selected from the group consisting of acetic acid, propionic acid, butyric acid, β-hydroxy-β-methylbutyric acid, valeric acid and salts, esters and mono-, di- and triglycerides thereof, for use in the treatment of disorders of the central nervous system (CNS).

Such CNS disorders are typically related to serotonin deficiency and are preferably selected among the group comprising epilepsy, neuropsychiatric disorders of Parkinson's disease and Huntington's chorea, depression, anxiety, dopamine-mimetic psychosis, emotional instability, compulsive-obsessive disorders, insomnia and cephalalgia.

It was, in fact, experimentally found that with the concomitant administration of alpha-lactalbumin and said short-chain fatty acid or a precursor or derivative thereof, a synergistic effect is achieved.

In one aspect of the present invention, the above-mentioned at least one short-chain fatty acid or a precursor or derivative thereof is contained in at least one first dosage unit together with a carrier acceptable from the pharmaceutical or food standpoint and the alpha-lactalbumin is contained in at least one second dosage unit together with a carrier acceptable from the pharmaceutical or food standpoint, said dosage units being distinct units intended for simultaneous or separate administration.

In another aspect, the pharmaceutical or food supplement preparation for the use according to the invention consists of a pharmaceutical or food supplement composition comprising the above-mentioned at least one short-chain fatty acid or a precursor or derivative thereof and the alpha-lactalbumin together with a carrier acceptable from the pharmaceutical or food standpoint.

Preferably, in the pharmaceutical or food supplement preparation according to both the above-mentioned aspects of the present invention, the alpha-lactalbumin is contained in an amount ranging from 0.1 to 2.0 g, more preferably from 0.3 to 1.0 g for each dose. It is possible to administer from 1 to 2 doses a day.

Preferably, the pharmaceutical or food supplement preparation for the use according to the present invention further contains magnesium and/or group B vitamins to promote the conversion of tryptophan into serotonin.

Alpha-lactalbumin of bovine origin is preferably used, not least by virtue of the fact that its amino acid composition is the most similar to the human one.

The composition or the dosage units according to the invention may be administered by various routes, although oral administration is preferred.

Preferably, the pharmaceutical or food supplement preparation according to the present invention is suitable for oral administration and is for example in the form of tablets, syrups, capsules, film coated tablets or sachets of powder or granules.

The above-mentioned at least one short-chain fatty acid or a precursor or derivative thereof contained in the pharmaceutical or food supplement preparation according to the present invention is preferably selected among the group comprising butyric acid and β-hydroxy-β-methylbutyric acid and alkaline or alkaline-earth salts thereof and esters thereof.

Among the esters of butyric acid particularly preferred are esters with glycerol, especially glyceryl tributyrate (tributyrin), glyceryl monobutyrate, ethyl butyryl lactate, pivaloyloxymethyl butyrate, 1-octyl butyrate, butyrate esters of carbohydrates and carbohydrate polyols.

Tributyrin may advantageously be used in form of a complex with a cyclodextrin, preferably as a 1:3 (weight ratio) tributyrin:gamma-cyclodextrin complex, to reduce the bitter taste and the unpleasant smell of tributyrin.

Preferably, the above-mentioned at least one short-chain fatty acid or derivative thereof is contained in the pharmaceutical or food supplement preparation according to the present invention in an amount ranging from 0.1 to 5.0 g, preferably from 0.2 to 1.0 g for each dose.

The present invention refers also to alpha-lactalbumin for use, in association with at least one short-chain fatty acid or a precursor or derivative thereof selected from the group consisting of acetic acid, propionic acid, butyric acid, β-hydroxy-β-methylbutyric acid, valeric acid and salts, esters and mono-, di- and triglycerides thereof, in the treatment of CNS disorders.

Such CNS disorders are typically related to serotonin deficiency and are preferably selected among the group comprising epilepsy, neuropsychiatric disorders of Parkinson's disease and Huntington's chorea, depression, anxiety, dopamine-mimetic psychosis, emotional instability, compulsive-obsessive disorders, insomnia and cephalalgia.

Finally, the present invention relates to a kit for use in the treatment of CNS disorders, including at least one first dosage unit containing at least one short-chain fatty acid or a precursor or derivative thereof, selected from the group consisting of acetic acid, propionic acid, butyric acid, β-hydroxy-β-methylbutyric acid, valeric acid and salts, esters and mono-, di- and triglycerides thereof, with a carrier acceptable from the pharmaceutical or food standpoint, and at least one second dosage unit containing α-lactalbumin, together with a carrier acceptable from the pharmaceutical or food standpoint, as well as instructions for the concomitant use of said at least one first and at least one second dosage unit in the treatment of the above-mentioned disorders.

Such CNS disorders are typically related to serotonin deficiency and are preferably selected among the group comprising epilepsy, neuropsychiatric disorders of Parkinson's disease and Huntington's chorea, depression, anxiety, dopamine-mimetic psychosis, emotional instability, compulsive-obsessive disorders, insomnia and cephalalgia.

The alpha-lactalbumin may be administered simultaneously with the short-chain fatty acid or a precursor or derivative thereof, for example by using pharmaceutical forms which contain both of the active ingredients or by simultaneously administering two pharmaceutical or food supplement forms of which one respectively contains alpha-lactalbumin and the other one the short-chain fatty acid or a precursor or derivative thereof. The two active ingredients may also be administered at different times over the course of the day on the basis of the dosage regimen specified by a doctor.

The present invention will be further described with reference to some examples which are provided by way of non-limiting illustration.

Example 1

| | |
|---|---|
| Purified bovine alpha-lactalbumin | 500 mg |
| β-hydroxy-β-methylbutyric acid | 500 mg |
| Mannitol | 50 mg |
| Flavoring agent | 10 mg |

The above-listed ingredients in powder form were mixed until homogeneous and sachets for oral administration were filled with the resultant mixture.

Example 2

| | |
|---|---|
| Purified bovine alpha-lactalbumin | 800 mg |
| Tributyrin | 300 mg |
| Anhydrous butter | 800 mg |
| Maltodextrins | 90 mg |
| Flavoring agent | 10 mg |

Alpha-lactalbumin was dispersed in distilled water (8% w/w) and kept under agitation for 60' at room temperature, then heated to 80° C. for 30' under agitation. The solution was then cooled and stored at 4° C. for 12 hours before being heated to 25° C. Melted anhydrous butter and tributyrin are added to this solution, forming an emulsion with the aid of a disperser (15000 rpm speed). The emulsion thereby obtained was homogenized by means of a two-stage homogenizer (1st stage 7 MPa; 2nd stage 55 MPa) and finally fed into a spray dryer (Buchi Mini Spray Dryer B-290), whose inlet temperature was maintained at 160° C. while the outlet temperature was 90° C., with a compressed air pressure equal to 552 kPa.

At the outlet of the spray dryer, spheroidal microcapsules, with an average diameter of about 4 μm, were obtained. The flavoring agent and maltodextrins were added to these microcapsules, inside a mixer, to obtain a uniform dispersion, which was then dosed in single-dose sachets.

Example 3

| Sachets of granules of sodium butyrate | |
|---|---|
| Sodium butyrate | 300.0 mg |
| Hydrogenated palm oil | 1500 mg |
| Calcium carbonate | 200 mg |
| Maltodextrins | 90 mg |
| Flavoring agent | 10 mg |

Granules of sodium butyrate microencapsulated in the hydrogenated palm oil were produced, adding sodium butyrate to the hydrogenated palm oil and to the calcium carbonate contained in a mixer heated to 70° C. and it was kept under agitation for about 15 minutes. The homogeneous mixture thereby obtained was sprayed by an appropriate nozzle inside a cooling chamber at about −10° C., thereby obtaining granules with a sodium butyrate-based inner core and a coating based on lipids and calcium carbonate. The granules thereby obtained were uniformly mixed with the remaining ingredients.

a Lactalbumin sachets:

| | |
|---|---|
| Purified bovine alpha-lactalbumin | 500 mg |
| Fructose | 200 mg |
| Flavoring agent | 10 mg |

The alpha-lactalbumin sachets and the sachets of granules of sodium butyrate were packaged in a paperboard box, into which was also introduced an information leaflet describing therapeutic indications, methods of taking the two sachets and posology.

The effects of the pharmaceutical preparation according to the present invention can be verified using the animal models of intestinal inflammation, which show a higher action of the formulation in reducing the inflammation on the inflammation induced by inflammatory agents such as for example Croton tiglium or dextran. Also intestinal inflammation markers, including PCR, calprotectin and the more specific NFkB p65/Beta Actin ratio, show the higher inflammation-reducing effect of the formulation according to the present invention compared also to the sum of the effects of the single components. The same markers may be also used in clinical studies to measure the action of reduction of inflammation. Intestinal inflammation measurements are currently performed also in studies on neurological and behavioral disorders, given the recent evidence of its common role in the pathogenetic mechanisms of different neurological and behavioral disorders. Interesting results obtained with feces transplant are reported about the latter, showing that an intestinal dysbiosis, induced by an inflammation, plays a fundamental role in these disorders. Our clinical data show a tight correlation between reduction of intestinal inflammation, wherein the most sensitive marker proved to be the Bristol Stool Chart test, and the reduction of cephalalgic attacks in adolescent cephalalgic subjects.

In addition, the effects of the pharmaceutical preparation according to the present invention can be verified by using the animal models commonly used for evaluating antidepressant agents, such as for example the forced swim test on rats according to Cristiano M. S. et al. ("Neonatal treatment with fluoxetine reduces depressive behaviour induced by forced swim in adult rats." Arq Neuropsiquiatr 2002; 60 (4): 928-932) or the forced swim test on mice according to Takahiro N. et al. ("Antidepressant-like effect of apignein and 2,4,5-trimethoxycinnamic acids from *Perilla frutescens* in the forced swimming test" Biol. Pharm. Bull. 2002; 26(4): 474-480) or finally the mouse model of chronic stress according to D'Aquila P. S. et al. ("Effects of chronic mild stress on performance in behavioral tests relevant to anxiety and depression". Physiol. Behav. 1994; 56 (5): 861-867).

Finally, the effects of the pharmaceutical preparation according to the present invention can be verified by using animal models commonly used for evaluating antiepileptic agents, such as for example the one disclosed in Russo E. et al., making use of the convulsant agent pentylenetetrazol [21].

Such effects have experimentally been verified and the results are reported in following Example 4.

Example 4

The anticonvulsant action of a preparation according to the invention, consisting of alpha-lactalbumin and sodium butyrate, was evaluated in comparison with that of the single components alpha-lactalbumin and sodium butyrate in the above-mentioned animal model, using the convulsant agent pentylenetetrazol The experiment was carried out on groups of 10 C57BL/6 male mice (Charles River Italy) for each tested dose (control groups of 10 C57BL/6 male mice were also used).

The animals of all groups were subcutaneously administered pentylenetetrazol (65 mg/kg) at the end of a 15-day pretreatment with sodium butyrate, alpha-lactalbumin, alpha-lactalbumin+sodium butyrate or vehicle, i.e. water (control), respectively.

This pretreatment was carried out by oral administration of a solution of either one of sodium butyrate, alpha-lactalbumin, alpha-lactalbumin+sodium butyrate in the vehicle, consisting of water, and of the vehicle (water) alone.

Firstly, three groups of 10 mice were orally administered 30 mg/day, 100 mg/day and 250 mg/day of sodium butyrate respectively, in the form of an aqueous solution contained in the bottle of the cage, for 15 days. The bottle of the cage of the control group (10 mice) only contained water.

On the 16th day, the animals of the four groups were subcutaneously administered 65 mg/kg of pentylenetetrazol. No significant difference was observed among the four groups, in that 100% of the animals of each group experienced seizures induced by pentylenetetrazol.

Then, three groups of 10 mice were orally administered 125 mg/day, 250 mg/day and 375 mg/day of alpha-lactalbumin respectively, in the form of an aqueous solution contained in the bottle of the cage, for 15 days. The bottle of the cage of the control group (10 mice) only contained water.

On the 16th day, the animals of the four groups were subcutaneously administered 65 mg/kg of pentylenetetrazol (PTZ).

As it can be appreciated from FIG. 1, left side, the percentage of animals with PTZ-induced seizures showed a decrease in a dose-dependent fashion, the greatest decrease being achieved with a dose of 375 mg/day of alpha-lactalbumin (less than 40% animals showing seizures).

Finally, a first group of 10 mice was orally administered 125 mg alpha-lactalbumin+100 mg sodium butyrate per day, a second group of 10 mice was orally administered 250 mg alpha-lactalbumin+100 mg sodium butyrate per day, a third group of 10 mice was orally administered 375 mg alpha-lactalbumin+100 mg sodium butyrate per day, in the form of an aqueous solution contained in the bottle of the cage, for 15 days. The bottle of the cage of the control group (10 mice) only contained water.

On the 16th day, the animals of the four groups were subcutaneously administered 65 mg/kg of pentylenetetrazol (PTZ).

FIG. 1, right side, shows a remarkable decrease of the percentage of mice with PTZ-induced seizures, the greatest decrease being achieved with a dose of 375 mg/day of alpha-lactalbumin+100 mg/day of sodium butyrate (less than 20% animals showing seizures). Furthermore, it can be observed, with respect to the values reported in the left side of FIG. 1, that the addition of 100 mg/day of sodium butyrate brings about a strong decrease of the percentage of animals with PTZ-induced seizures at each dose of alpha-lactalbumin. In particular, it is noteworthy that a dose of 125 mg/day of alpha-lactalbumin, which does not significantly decrease the percentage of mice with PTZ-induced seizures, when administered together with a dose of 100 mg/day of sodium butyrate, does significantly reduce such percentage This is totally unexpected, considering that sodium butyrate was found to be devoid of any activity towards the seizures induced by pentylenetetrazol.

REFERENCES

1) Derek A. Mann e Fiona Oakley, Serotonin paracrine signaling in tissue fibrosis, in Biochimica et Biophysica Acta, vol. 1832, no 7, 2013-7, pp. 905-910);

2) Clifford J Rosen, "Breaking into bone biology: serotonin's secrets", in Nature Medicine, vol. 15, no 2, pp. 145-146;

3) Ramadhan B. Matondo, Carine Punt e Judith Homberg, "Deletion of the serotonin transporter in rats disturbs serotonin homeostasis without impairing liver regeneration", in American Journal of Physiology—Gastrointestinal and Liver Physiology, vol. 296, no 4, 1° aprile 2009, pp. G963-G968, 4) Marieb, Elaine Nicpon, 1936-, "Essentials of human anatomy & physiology", 9th ed, Pearson/Benjamin Cummings, 2009.

5) Jobe P C. Affective disorder and epilepsy comorbidity: implications for development of treatments, preventions and diagnostic approaches. Clin EEG Neurosci. 2004 January; 35(1):53-68

6) Statnick M A, Maring-Smith M L, Clough R W, Wang C, Dailey J W, Jobe P C, Browning R A. Effect of 5,7-dihydroxytryptamine on audiogenic seizures in genetically epilepsy-prone rats. Life Sci. 1996; 59(21):1763-71.

7) Jobe P C, Browning R A. The serotonergic and noradrenergic effects of antidepressant drugs are anticonvulsant, not proconvulsant. Epilepsy Behav. 2005 December; 7(4): 602-19

8) Favale E, Rubino V, Mainardi P, Lunardi G, Albano C. Anticonvulsant effect of fluoxetine in humans. Neurology. 1995 October; 45(10):1926-7.

9) Albano C, Cupello A, Mainardi P, Scarrone S, Favale E. Successful treatment of epilepsy with serotonin reuptake inhibitors: proposed mechanism. Neurochem Res. 2006 April; 31(4):509-14

10) Jobe P C. Common pathogenic mechanisms between depression and epilepsy: an experimental perspective. Epilepsy Behav. 2003 October; 4 Suppl 3:S14-24.

11) Jobe P C, Dailey J W, Wernicke J F. A noradrenergic and serotonergic hypothesis of the linkage between epilepsy and affective disorders. Crit Rev Neurobiol. 1999; 13(4): 317-56

12) Jobe P C. Shared mechanisms of antidepressant and antiepileptic treatments: drugs and devices. Clin EEG Neurosci. 2004 January; 35(1):25-37.

13) Mainardi P, Leonardi A, Albano C. Potentiation of brain serotonin activity may inhibit seizures, especially in drug-resistant epilepsy. Med Hypotheses. 2008; 70(4):876-9.

14) Fernstrom J D, Wurtman R J. Brain serotonin content: physiological regulation by plasma neutral amino acids. Science. 1972 Oct. 27; 178(4059):414-6.

15) Lunardi G, Mainardi P, Rubino V, Fracassi M, Pioli F, Cultrera S, Albano C. Tryptophan and epilepsy. Adv Exp Med Biol. 1996; 398:101-2.

16) Heuther G, Hajak G, Reimer A, Poeggeler B, Biamer M, Rodenbeck A, Rather E. The metabolic fate of infused L-tryptophan in men: possible clinical implications of the accumulation of circulating tryptophan and tryptophan metabolites. Psychopharmacology (Berl). 1992; 109(4):422-32.

17) Frenhani P B, Burini R C. Mechanism of action and control in the digestion of proteins and peptides in humans. Arq Gastroenterol. 1999 July-September; 36(3): 139-47

18) Markus C R, Klöpping-Ketelaars W I, Pasman W, Klarenbeek B, van den Berg H. Dose-Dependent Effect of α-Lactalbumin in Combination with Two Different Doses of Glucose on the Plasma Trp/LNAA Ratio. Nutr Neurosci. 2000; 3 (5): 345-55.

19) Feurté, Sébastien & Gerozissis, Kyriaki & Regnault, Alain & M. Paul, François. (2001). Plasma Trp/LNAA Ratio Increases During Chronic Ingestion of An alpha-lactalbumin Diet in Rats. Nutritional neuroscience. 4. 413-8.

20) Citraro R, Scicchitano F, De Fazio S, Raggio R, Mainardi P, Perucca E, De Sarro G, Russo E. Preclinical activity profile of α-lactoalbumin, a whey protein rich in tryptophan, in rodent models of seizures and epilepsy. Epilepsy Res. 2011 June; 95 (1-2): 60-9.

21) Russo E, Scicchitano F, Citraro R, Aiello R, Camastra C, Mainardi P, Chimirri S, Perucca E, Donato G, De Sarro G. Protective activity of α-lactoalbumin (ALAC), a whey protein rich in tryptophan, in rodent models of epileptogenesis. Neuroscience. 2012 Dec. 13; 226:282-8

22) Ushida Y, Shimokawa Y, Matsumoto H, Toida T, Hayasawa H. Effects of bovine alpha-lactalbumin on gastric defense mechanisms in naive rats. Biosci Biotechnol Biochem. 2003 March; 67(3):577-83

23) Matsumoto H, Shimokawa Y, Ushida Y, Toida T, Hayasawa H. New biological function of bovine alpha-lactalbumin: protective effect against ethanol- and stress-induced gastric mucosal injury in rats. Biosci Biotechnol Biochem. 2001 May; 65(5):1104-11

24) Rusu D, Drouin R, Pouliot Y, Gauthier S, Poubelle P E. A bovine whey protein extract stimulates human neutrophils to generate bioactive IL-1Ra through a NF-kappaB- and MAPK-dependent mechanism. J Nutr. 2010 February; 140(2):382-91

25) Pellegrini A, Thomas U, Bramaz N, Hunziker P, von Fellenberg R. Isolation and identification of three bactericidal domains in the bovine alpha-lactalbumin molecule. Biochim Biophys Acta. 1999 Feb. 2; 1426(3):439-48

26) Marja-Leena Koskiniemi, Journal of the Neurological Sciences, Volume 47, Issue 1, July 1980, Pages 1-6)

27) Fukumoto, S., Tatewaki, M., Yamada, T., Fujimiya, M., Mantyh, C., Voss, M., Eubanks, S., Harris, M., Pappas, T. N., Takahashi, T., 2003. Short-chain fatty acids stimulate colonic transit via intraluminal 5-HT release in rats. Am. J. Physiol. Regul. Integr. Comp. Physiol. 284, R1269eR1276

28) Davie J R. Inhibition of histone deacetylase activity by butyrate. J Nutr. 2003 July; 133 (7 Suppl): 2485S-2493S 29) Vinolo M A, Rodrigues H G, Nachbar R T, Curi R. Regulation of inflammation by short chain fatty acids. Nutrients. 2011 October; 3(10):858-76

30) Sekirov I, Russell S L, Antunes L C, Finlay B B. Gut microbiota in health and disease. Physiol Rev. 2010 July; 90(3):859-904

31) Richards J L, Yap Y A, McLeod K H, Mackay C R, Marino E. Dietary metabolites and the gut microbiota: an alternative approach to control inflammatory and autoimmune diseases. Clin Transl Immunology. 2016 May 13; 5 (5): e82.

32) Corrêa R O, Vieira A, Sernaglia E M, Lancellotti M, Vieira A T, Avila-Campos M J, Rodrigues H G, Vinolo M A. Bacterial short-chain fatty acid metabolites modulate the inflammatory response against infectious bacteria. Cell Microbiol. 2017 July; 19 (7)

33) Han R, Sun Q, Wu J, Zheng P, Zhao G. Sodium Butyrate Upregulates miR-203 Expression to Exert Anti-Proliferation Effect on Colorectal Cancer Cells. Cell Physiol Biochem. 2016; 39(5):1919-1929.

34) Khan S, Jena G. Sodium butyrate reduces insulin-resistance, fat accumulation and dyslipidemia in type-2 diabetic rat: A comparative study with metformin. Chem Biol Interact. 2016 Jul. 25; 254:124-34

35) Khan S, Jena G. The role of butyrate, a histone deacetylase inhibitor in diabetes mellitus: experimental evidence for therapeutic intervention. Epigenomics. 2015; 7(4): 669-80.

36) Newman J C, Verdin E. β-hydroxybutyrate: much more than a metabolite. Diabetes Res Clin Pract. 2014 November; 106(2):173-81

37) Butchbach M E, Lumpkin C J, Harris A W, Saieva L, Edwards J D, Workman E, Simard L R, Pellizzoni L, Burghes A H. Protective effects of butyrate-based compounds on a mouse model for spinal muscular atrophy. Exp Neurol. 2016 May; 279:13-26.

38) Walsh M E, Bhattacharya A, Sataranatarajan K, Qaisar R, Sloane L, Rahman M M, Kinter M, Van Remmen H. The histone deacetylase inhibitor butyrate improves metabolism and reduces muscle atrophy during aging. Aging Cell. 2015 December; 14(6):957-70.

39) Wang J, Wen L, Wang Y, Chen F. Therapeutic Effect of Histone Deacetylase Inhibitor, Sodium Butyrate, on Allergic Rhinitis In Vivo. DNA Cell Biol. 2016 April; 35(4): 203-8

40) Chen Y, Du J, Zhao Y T, Zhang L, Lv G, Zhuang S, Qin G, Zhao T C. Histone deacetylase (HDAC) inhibition improves myocardial function and prevents cardiac remodeling in diabetic mice. Cardiovasc Diabetol. 2015 Aug. 7; 14:99

41) Simon-O'Brien E, Alaux-Cantin S, Warnault V, Buttolo R, Naassila M, Vilpoux C. The histone deacetylase inhibitor sodium butyrate decreases excessive ethanol intake in dependent animals. Addict Biol. 2015 July; 20(4):676-89.

42) Liang X, Wang R S, Wang F, Liu S, Guo F, Sun L, Wang Y J, Sun Y X, Chen X L. Sodium butyrate protects against severe burn-induced remote acute lung injury in rats. PLoS One. 2013 Jul. 11; 8 (7): e68786

43) Mishiro T, Kusunoki R, Otani A, Ansary M M, Tongu M, Harashima N, Yamada T, Sato S, Amano Y, Itoh K, Ishihara S, Kinoshita Y. Butyric acid attenuates intestinal inflammation in murine DSS-induced colitis model via milk fat globule-EGF factor 8. Lab Invest. 2013 July; 93(7):834-43.

44) Arpaia N, Rudensky A Y. Microbial metabolites control gut inflammatory responses. Proc Natl Acad Sci USA. 2014 Feb. 11; 111(6):2058-9.

45) Resende W R, Valvassori S S, Réus G Z, Varela R B, Arent C O, Ribeiro K F, Bavaresco D V, Andersen M L, Zugno A I, Quevedo J. Effects of sodium butyrate in animal models of mania and depression: implications as a new mood stabilizer. Behav Pharmacol. 2013 October; 24(7): 569-79

46) Pandey K, Sharma K P, Sharma S K. Histone deacetylase inhibition facilitates massed pattern-induced synaptic plasticity and memory. Learn Mem. 2015 Sep. 15; 22(10): 514-8.

47) Valvassori S S, Varela R B, Arent C O, Dal-Pont G C, Bobsin T S, Budni J, Reus G Z, Quevedo J. Sodium butyrate functions as an antidepressant and improves cognition with enhanced neurotrophic expression in models of maternal deprivation and chronic mild stress. Curr Neurovasc Res. 2014; 11(4):359-66.

48) Blank M, Werenicz A, Velho L A, Pinto D F, Fedi A C, Lopes M W, Peres T V, Leal R B, Dornelles A S, Roesler R. Enhancement of memory consolidation by the histone deacetylase inhibitor sodium butyrate in aged rats. Neurosci Lett. 2015 May 6; 594:76-81

49) Gagliano H, Delgado-Morales R, Sanz-Garcia A, Armario A. High doses of the histone deacetylase inhibitor sodium butyrate trigger a stress-like response. Neuropharmacology. 2014 April; 79:75-82

50) Kratsman N, Getselter D, Elliott E. Sodium butyrate attenuates social behavior deficits and modifies the transcription of inhibitory/excitatory genes in the frontal cortex of an autism model. Neuropharmacology. 2016 March; 102: 136-45.

51) Valvassori S S, Dal-Pont G C, Steckert A V, Varela R B, Lopes-Borges J, Mariot E, Resende W R, Arent C O, Carvalho A F, Quevedo J. Sodium butyrate has an antimanic effect and protects the brain against oxidative stress in an animal model of mania induced by ouabain. Psychiatry Res. 2016 Jan. 30; 235:154-9.

52) Kim, S. W., Hooker, J. M., Otto, N., Win, K., Muench, L., Shea, C., Carter, P., King, P., Reid, A. E., Volkow, N. D., Fowler, J. S., 2013. Whole-body pharmacokinetics of HDAC inhibitor drugs, butyric acid, valproic acid and 4-phenylbutyric acid measured with carbon-11 labeled analogs by PET. Nucl. Med. Biol. 40, 912e918

53) Schroeder, F. A., Lin, C. L., Crusio, W. E., Akbarian, S., 2007. Antidepressant-like effects of the histone deacetylase inhibitor, sodium butyrate, in the mouse. Biol. Psychiatry 62, 55e64

54) Wei, Y., Melas, P. A., Wegener, G., Mathe, A. A., Lavebratt, C., 2015. Antidepressant-like effect of sodium butyrate is associated with an increase in TET1 and in 5-hydroxymethylation levels in the Bdnf gene. Int. J. Neuropsychopharmacol. Off. Sci. J. Coll. Int. Neuropsychopharmacol. CINP 18.

55) Intlekofer, K. A., Berchtold, N. C., Malvaez, M., Carlos, A. J., McQuown, S. C., Cunningham, M. J., Wood, M. A., Cotman, C. W., 2013. Exercise and sodium butyrate transform a subthreshold learning event into long-term memory via a brain-derived neurotrophic factor-dependent mechanism. Neuropsychopharmacol. Off. Publ. Am. Coll. Neuropsychopharmacol. 38, 2027e2034.

56) Riazi K, Galic M A, Pittman Q J. Contributions of peripheral inflammation to seizure susceptibility: cytokines and brain excitability. Epilepsy Res. 2010 March; 89(1):34-42.9

57) Chow J, Lee S M, Shen Y, Khosravi A, Mazmanian S K. Host-bacterial symbiosis in health and diseases. Adv. Immunol. 2010; 107:243-74

The invention claimed is:

1. A method of treating disorders of the central nervous system (CNS) in a subject in need thereof, comprising administering to said subject a pharmaceutical or food supplement preparation including α-lactalbumin and at least one short-chain fatty acid or a precursor or derivative thereof selected from the group consisting of propionic acid, butyric acid, β-hydroxy-β-methylbutyric acid, valeric acid and salts, esters and mono-, di- and triglycerides thereof.

2. The method according to claim 1, wherein said CNS disorders are CNS disorders related to serotonin deficiency.

3. The method according to claim 2, wherein said CNS disorders related to serotonin deficiencies are selected among the group consisting of epilepsy, neuropsychiatric disorders of Parkinson's disease and Huntington's chorea, depression, anxiety, dopamine-mimetic psychosis, emotional instability, compulsive-obsessive disorders, insomnia and cephalalgia.

4. The method according to claim 2, wherein said at least one short-chain fatty acid or a precursor or derivative thereof is contained in at least one first dosage unit together with a carrier acceptable from the pharmaceutical or food standpoint and the α-lactalbumin is contained in at least one second dosage unit together with a carrier acceptable from the pharmaceutical or food standpoint, said dosage units being distinct units intended for simultaneous or separate administration.

5. The method according claim 2, wherein said pharmaceutical or food supplement preparation consists of a pharmaceutical or food supplement composition comprising said at least one short-chain fatty acid or a precursor or a derivative thereof and said α-lactalbumin together with a carrier acceptable from the pharmaceutical or food standpoint.

6. The method according to claim 4, wherein the α-lactalbumin is contained in said at least one second dosage unit in an amount ranging from 0.1 to 2.0 g.

7. The method according to claim 5, wherein the α-lactalbumin is contained in said pharmaceutical or food supplement composition in an amount ranging from 0.1 to 2.0 g.

8. The method according to claim 4, wherein said at least one second dosage unit further contains magnesium and/or group B vitamins.

9. The method according to claim 6, wherein said at least one second dosage unit further contains magnesium and/or group B vitamins.

10. The method of claim 5, wherein said pharmaceutical or food supplement composition further comprises magnesium and/or group B vitamins.

11. The method of claim 7, wherein said pharmaceutical or food supplement composition further comprises magnesium and/or group B vitamins.

12. The method of claim 2, wherein said preparation is suitable for an oral administration.

13. The method of claim 5, wherein said pharmaceutical or food supplement composition is in the form of tablets, syrups, capsules, film coated tablets or sachets of powder or granules.

14. The method of claim 4, wherein said at least one first and at least one second dosage units are independently in the form of tablets, capsules, film coated tablets or sachets of powder or granules.

15. The method of claim 2, wherein said at least one short-chain fatty acid or a precursor or derivative thereof is selected among the group consisting of butyric acid and β-hydroxy-β-methylbutyric acid and alkaline or alkaline-earth salts thereof and esters with glycerol thereof.

16. The method of claim 2, wherein said at least one short-chain fatty acid or a precursor or derivative thereof is selected among the group consisting of sodium butyrate, glyceryl tributyrate, glyceryl monobutyrate, butyrate esters of carbohydrates and carbohydrate polyols.

17. The method of claim 15, wherein said at least one short-chain fatty acid or a precursor or derivative thereof is contained in an amount ranging from 0.1 to 5.0 g.

18. The method of claim 17, wherein said at least one short-chain fatty acid or a precursor or derivative thereof is contained in an amount ranging from 0.2 to 1.0 g.

* * * * *